United States Patent
Reinecke (10) Patent No.: US 6,997,892 B2
(45) Date of Patent: *Feb. 14, 2006

(54) AMBULATORY CYCLIC TRACTION DEVICE

(75) Inventor: Steven M. Reinecke, Dallas, TX (US)

(73) Assignee: AMEI Technologies, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 10/370,823

(22) Filed: Feb. 20, 2003

(65) Prior Publication Data

US 2004/0077982 A1    Apr. 22, 2004

Related U.S. Application Data

(60) Provisional application No. 60/419,767, filed on Oct. 17, 2002.

(51) Int. Cl.
A61F 5/00        (2006.01)

(52) U.S. Cl. ............................. 602/32; 602/19; 602/36

(58) Field of Classification Search ............... 602/5, 602/16, 19, 32, 36, 38, 60, 61; 606/237, 606/240–242; 128/874–876; 482/124, 128
See application file for complete search history.

(56) References Cited

U.S. PATENT DOCUMENTS

| | | | |
|---|---|---|---|
| 1,589,670 A | 6/1926 | Vartia | |
| 2,835,247 A | 5/1958 | Stabholc | 128/78 |
| 3,029,810 A | 8/1962 | Martin | 128/78 |
| 3,351,053 A | 11/1967 | Stuttle | 128/78 |
| 3,420,230 A | 1/1969 | Ballard | 128/75 |
| 3,521,623 A | 7/1970 | Nichols et al. | 128/78 |
| 3,548,817 A | 12/1970 | Mittasch | 128/75 |
| 3,598,114 A | 8/1971 | Lewis | 128/78 |
| 3,889,664 A | 6/1975 | Heuser et al. | 128/75 |
| 3,926,182 A | 12/1975 | Stabholz | 128/75 |
| 4,135,503 A | 1/1979 | Romano | 128/78 |
| 4,269,179 A | 5/1981 | Burton et al. | 128/75 |
| 4,497,517 A | 2/1985 | Gmeiner et al. | 297/231 |
| 4,552,135 A | 11/1985 | Racz et al. | 128/78 |
| 4,559,933 A | 12/1985 | Batard et al. | 128/78 |
| 4,583,532 A * | 4/1986 | Jones | 602/32 |
| 4,599,998 A | 7/1986 | Castillo | 128/77 |
| 4,622,957 A | 11/1986 | Curlee | 128/78 |

(Continued)

FOREIGN PATENT DOCUMENTS

CH        0689797 A      11/1999

(Continued)

OTHER PUBLICATIONS

Unknown, "Office, Computer and Industrial Ergonomics," AliMed, Dedham, Massachusetts, 2 page brochure, 1993.

(Continued)

Primary Examiner—Michael A. Brown
Assistant Examiner—Quang D. Thanh
(74) Attorney, Agent, or Firm—Baker & McKenzie (57) ABSTRACT

In one embodiment, an ambulatory cyclic traction device includes two support belts configured to be positioned about a user's body and one or more lifting mechanisms coupled between the support belts, the one or more lifting mechanisms adapted to apply a decompressive force to a portion of the user's body between the support belts. A control system is operable to automatically cause the one or more lifting mechanisms to cyclically apply the decompressive force to the portion of the user's body through the support belts when the support belts are positioned about the user's body, such that the decompressive force is applied for a predetermined time interval during each of a series of traction cycles.

35 Claims, 7 Drawing Sheets

U.S. PATENT DOCUMENTS

| | | | | |
|---|---|---|---|---|
| 4,682,588 A | | 7/1987 | Curlee | 128/78 |
| 4,685,668 A | | 8/1987 | Newlin, Jr. | 272/123 |
| 4,691,696 A | | 9/1987 | Farfan de los Godos | 128/78 |
| 4,702,235 A | | 10/1987 | Hong | 128/78 |
| 4,715,362 A | | 12/1987 | Scott | 128/75 |
| 4,721,102 A | | 1/1988 | Pethybridge | 128/78 |
| 4,836,194 A | | 6/1989 | Sebastian et al. | 128/78 |
| 4,884,562 A | | 12/1989 | Stone | 128/78 |
| 4,898,185 A | | 2/1990 | Fuller | 128/876 |
| 4,907,575 A | | 3/1990 | Satterthwaite | 128/75 |
| 4,991,572 A | | 2/1991 | Chases | 128/75 |
| 4,991,573 A | | 2/1991 | Miller | 128/78 |
| 5,060,640 A | | 10/1991 | Rasmusson | 128/80 C |
| 5,062,414 A | | 11/1991 | Grim | 128/68.1 |
| 5,111,807 A | | 5/1992 | Spahn et al. | 606/244 |
| 5,144,943 A | | 9/1992 | Luttrell et al. | 128/25 B |
| 5,188,586 A | | 2/1993 | Castel et al. | 602/19 |
| 5,207,635 A | | 5/1993 | Richards et al. | 602/19 |
| 5,224,924 A | * | 7/1993 | Urso | 602/19 |
| 5,256,135 A | | 10/1993 | Avihod | 602/19 |
| 5,363,863 A | | 11/1994 | Lelli et al. | 128/876 |
| 5,382,226 A | | 1/1995 | Graham | 602/32 |
| 5,403,266 A | | 4/1995 | Bragg et al. | 602/5 |
| 5,437,617 A | | 8/1995 | Heinz et al. | 602/19 |
| 5,441,479 A | | 8/1995 | Chitwood | 602/18 |
| 5,462,518 A | | 10/1995 | Hatley et al. | 602/36 |
| 5,586,969 A | | 12/1996 | Yewer, Jr. | 602/19 |
| 5,651,764 A | | 7/1997 | Chiu | 602/36 |
| 5,681,267 A | | 10/1997 | Molino et al. | 602/19 |
| 5,690,609 A | | 11/1997 | Heinze, III | 602/19 |
| 5,704,904 A | * | 1/1998 | Dunfee | 602/13 |
| 5,722,940 A | | 3/1998 | Gaylord, Jr. et al. | 602/19 |
| 5,913,410 A | | 6/1999 | Tsuchiya | 2/311 |
| 5,916,188 A | | 6/1999 | Ousdal | 602/32 |
| 6,099,490 A | | 8/2000 | Turtzo | 602/19 |
| 6,146,345 A | | 11/2000 | Mignard | 602/19 |
| 6,533,740 B2 | | 3/2003 | Reinecke et al. | 602/5 |
| 6,540,707 B1 | * | 4/2003 | Stark et al. | 602/13 |
| 6,689,082 B2 | * | 2/2004 | Reinecke et al. | 602/32 |
| 6,702,771 B1 | * | 3/2004 | Reinecke et al. | 602/19 |

FOREIGN PATENT DOCUMENTS

| | | |
|---|---|---|
| CH | 0690398 A | 8/2000 |
| DE | 2637244 A1 | 6/1977 |
| DE | 19610018 A1 | 10/1996 |
| DE | 10007634 A1 | 7/2001 |
| DE | 10007635 A1 | 7/2001 |
| EP | 0864308 A1 | 9/1998 |
| WO | WO 02/069858 A1 | 9/2002 |

OTHER PUBLICATIONS

Unknown, "1992 Catalog," The Saunders Group, Inc., brochure, 2 pages, 1992.

Reinecke et al., "Traction Device," U.S. Appl. No. 09/875,486, pending, Jun. 5, 2001.

Reinecke et al., "Canting Mechanism for an Ambulatory Support Device," U.S. Appl. No. 09/875,473, pending, Jun. 5, 2001.

Reinecke et al., "Traction Device Adjustment Mechanism and Method," U.S. Appl. No. 09/875,315, pending, Jun. 5, 2001.

Reinecke et al., "Measurement Device for Fitting a Bracing Device," U.S. Appl. No. 10/154,695, pending, May 23, 2002.

Reinecke, et al., "Dynamically Adjustable Stabilization Brace," U.S. Appl. No. 10/407,052, pending, Apr. 3, 2003.

Reinecke, et al., "Traction Device and Associated Lifting Mechanisms," U.S. Appl. No. 10/335,694, pending, Jan. 2, 2003.

PCT, Notification of Transmittal of the International Search Report or the Declaration, 7 pages, Apr. 7, 2002.

PCT, Notification of Transmittal of the International Search Report or the Declaration, 6 pages, Jan. 31, 2003.

PCT, Notification of International Search Report or the Declaration and International Search Report for PCT/US03/32266, Sep. 3, 2004, 4 pages.

* cited by examiner

AMBULATORY CYCLIC TRACTION DEVICE

RELATED APPLICATION

This application claims the benefit under 35 U.S.C. § 119(e) of U.S. Provisional Application Ser. No. 60/419,767 filed Oct. 17, 2002 entitled "Ambulatory Traction Device and Method for Using Same."

TECHNICAL FIELD OF THE INVENTION

This invention relates to the field of medical devices and, more particularly, to an ambulatory cyclic traction device.

BACKGROUND OF THE INVENTION

People have long dealt with the pain, aggravation, and loss of productivity arising from bodily injuries, such as those to the back, neck, knees, and elbows. In fact, most people will at some point in their lives be incapacitated by back pain, particularly low back pain. The relative case with which injuries to the back and other portions of the body are incurred merely adds to the overall severity of the problem. The forms of treatment vary over the length of time that a patient experiences pain. For example, eighty percent of low back pain sufferers heal over the course of six weeks with minimal intervention. However, the remaining twenty percent of sufferers create the greatest challenges and cost to the medical system. After the acute phase, surgical intervention or more invasive forms of treatment may be selected, but minimally-invasive or non-invasive treatment methods are preferred where appropriate. Another concern when dealing with bodily injuries is rehabilitation. Because injuries to the back, neck, knees, elbows, and other portions of the body do not typically heal in a matter of days, effective rehabilitation techniques are important for successful healing and recovery.

SUMMARY OF THE INVENTION

According to the present invention, problems and disadvantages associated with previous rehabilitation technique may be reduced or eliminated.

In one embodiment, an ambulatory cyclic traction device includes two support belts configured to be positioned about a user's body and one or more lifting mechanisms coupled between the support belts, the one or more lifting mechanisms adapted to apply a decompressive force to a portion of the user's body between the support belts. A control system is operable to automatically cause the one or more lifting mechanisms to cyclically apply the decompressive force to the portion of the user's body through the support belts when the support belts are positioned about the user's body, such that the decompressive force is applied for a predetermined time interval during each of a series of traction cycles.

Particular embodiments of the present invention provide one or more technical advantages. For example, certain embodiments may provide a traction device that may be worn by a user to cyclically reduce the compressive forces on the user's spine or other body part by cyclically transferring at least a portion of the user's upper body weight off of the spine or other body part to the surrounding areas for a series predetermined time intervals. In particular, the decompressive forces generated by the traction device may be concentrated on the lower spine of the user, an area that may be commonly injured due to compressive forces. The traction device may also provide stabilization of the torso to prevent additional compressive forces in the spine due to bending and lifting by the user. Moreover, in certain embodiments, an ambulatory cyclic traction device may be used in association with other joints of the body, such as the neck, knee, or elbow. Furthermore, certain embodiments may provide a traction device that is ambulatory, meaning that the device is portable and wearable during the user's daily activities. The ambulatory nature of the traction device provides more convenience to the user, causes less impact on the user's daily activities, and may lead to quicker healing and recovery than treatment techniques in which the spine or other portion of the body is substantially immobilized. Certain embodiments may provide all, some, or none of these advantages. Certain embodiments may provide one or more other technical advantages, one or more of which may be readily apparent to those skilled in the art from the figures, descriptions, and claims included herein.

BRIEF DESCRIPTION OF THE DRAWINGS

To provide a more complete understanding of the present invention and the features and advantages thereof, reference is made to the following description taken in conjunction with the accompanying drawings, in which.

DESCRIPTION OF EXAMPLE EMBODIMENTS

Figure 1A:
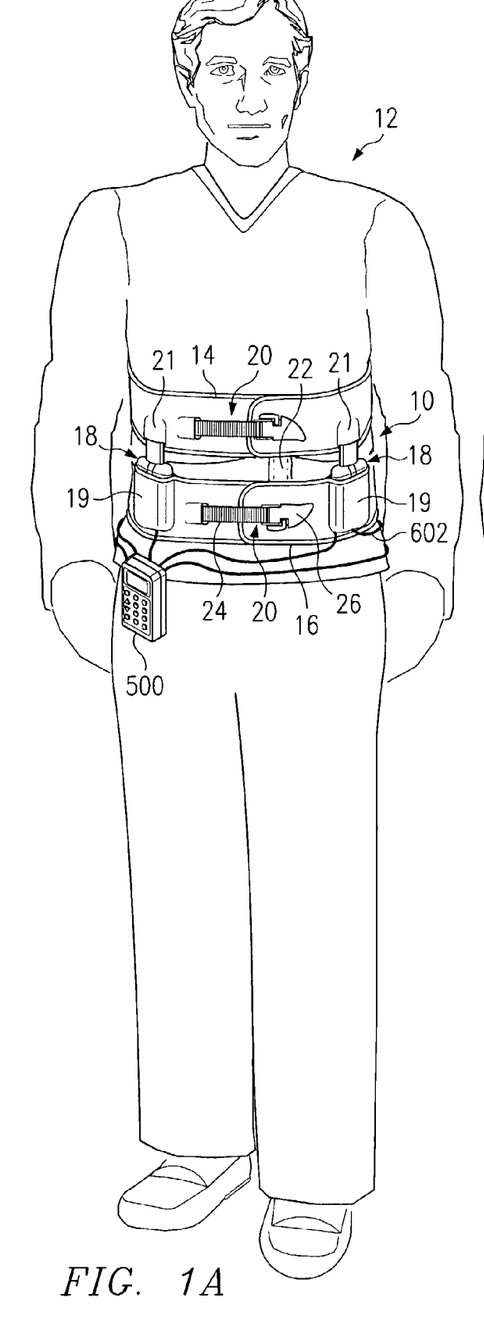
FIGS. 1A and 1B illustrate a user wearing an example ambulatory cyclic traction device.
Figure 1B:
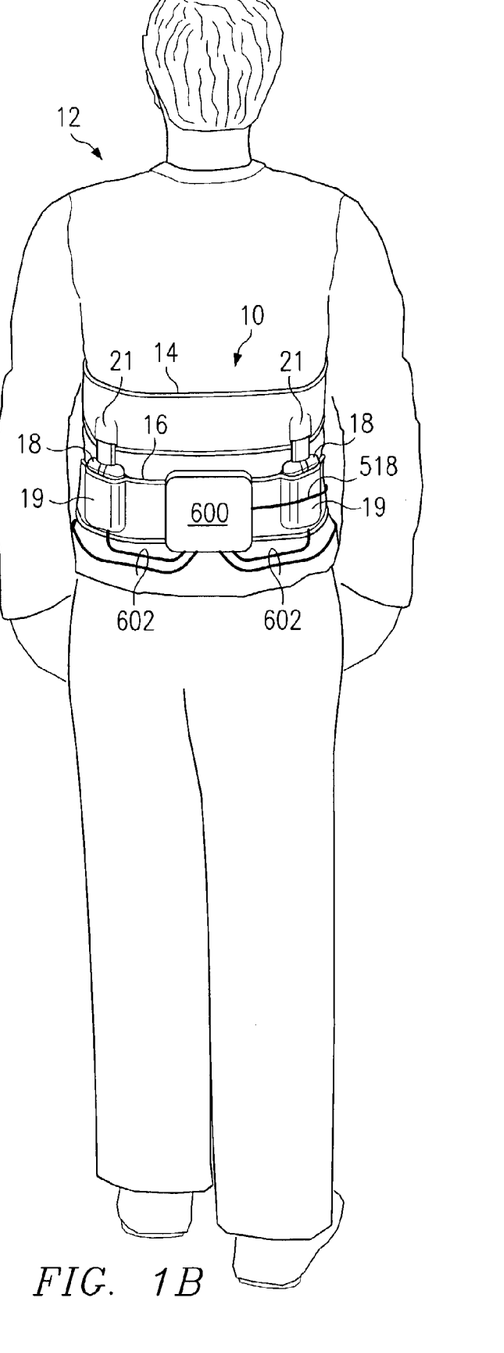

FIGS. 1A and 1B illustrate a user 12 wearing an ambulatory cyclic traction device 10 constructed according to one embodiment of the present invention. In the illustrated embodiment, traction device 10 applies decompressive forces to the spine of user 12. In other embodiments, traction device 10 applies decompressive forces to other portions of the user's body, such as the neck, knee, elbow, or other joint. In the illustrated embodiment, the decompressive forces transfer body weight from the spine to the hips of user 12 to reduce compression and aggravation of low back injuries or other conditions. Decompressive forces are created by traction device 10 as described below.

Traction device 10 includes an upper support belt 14 and a lower support belt 16. Support belts 14, 16 may be formed in any suitable manner that allows them to be positioned around a desired portion of the user's body and to thereafter transfer a decompressive force to that portion of the user's body. Example details of one embodiment of support belts 14, 16 are described in greater detail below with reference to FIG. 3.

Traction device 10 also includes one or more lifting mechanisms 18. Example details associated with one embodiment of a lifting mechanism 18 are described below with reference to FIGS. 5A through 5D. In the illustrated embodiment, lifting mechanisms 18 are fluidic (for example, pneumatic or hydraulic) devices that create decompressive, or tensile, forces with respect to a portion of the user's body through fluid pressure supplied by an actuator system 600 and controlled by an operator control unit 500. When pressurized, lifting mechanisms 18 push upward on support belt 14 and downward on support belt 16, resulting in a decompressive force on the spine of user 12. In alternative embodiments, lifting mechanisms 18 may be mechanical or electromechanical devices. Lifting mechanisms 18 may be coupled to support belts 14, 16 as described below with reference to FIG. 4. Lifting mechanisms 18 may be disposed and at least partially concealed within pouches 19 connected to support belt 16 and pouches 21 connected to support belt 14. Example locations of lifting mechanisms 18 about the circumference of a support belts 14, 16 are shown more clearly in FIGS. 2A and 2B.

Traction device 10 further includes operator control unit 500 (described more fully below with reference to FIG. 5) and actuator system 600 (described more fully below with reference to FIG. 6) coupled to lifting mechanisms 18. Lifting mechanisms 18, operator control unit 500, and actuator system 600 work in conjunction with one another to generate decompressive, or tensile, forces that may be transferred to a portion of the user's body through support belts 14, 16. Generally, operator control unit 500 controls the fluid pressure in lifting mechanisms 18 by directing the elements of actuator system 600 to transport fluid to and from lifting mechanisms 18 via one or more tubes or other conduits 602 associated with lifting mechanisms 18. In certain embodiments, as described more fully below, operator control unit 500 works in conjunction with actuator system 600 to provide cyclic traction to user 12. As illustrated in FIGS. 1A and 1B, operator control unit 500 may be coupled to the front of user 12 just below support belt 16 and actuator system 600 may be coupled to support belt 16 at the rear of user 12. However, both operator control unit 500 and actuator system 600 may be coupled to user 12 and/or support belts 14, 16 at any suitable location and in any suitable manner. Furthermore, although shown as separate components, operator control unit 500 and actuator system 600 may be integrated. Operator control unit 500 and actuator system 600 may be collectively referred to herein as a control system.

A proper fitting of traction device 10 about the body of user 12 is important. Fitting may be accomplished, in part, using a pair of locking mechanisms 20, one located on support belt 14 and one located on support belt 16, and a common strap 22. In one embodiment, common strap 22 forms a part of both support belts 14, 16 and therefore allows substantially equivalent adjustment of both support belts 14, 16 at substantially the same time. Each locking mechanism 20 includes a number of notches 24 and a latch 26 for securing locking mechanism 20 in place at a desired notch location. Locking mechanism 20 may be replaced with any suitable mechanism for securing support belts 14, 16 in a desired position, such as snaps, hook and loop type fasteners, or other suitable fasteners Common strap 22 is described in greater detail below with reference to FIG. 3.

In one embodiment, user 12 places traction device 10 around the user's torso, for example, with support belt 14 below the ribs and support belt 16 above the hips. User 12 adjusts support belts 14, 16 to a desired tension using common strap 22, which may be referred to as macro-adjustment of traction device 10. Common strap 22 may facilitate substantially equivalent and substantially simultaneous adjustment of support belts 14, 16. User 12 may then adjust and secure support belts 14, 16 in place using locking mechanisms 20, which may be referred to as micro-adjustment of traction device 10. To apply traction to the user's spine, an appropriate person, such as user 12, may use operator control unit 500 to input traction parameters, such as the desired amount of traction, the number of traction cycles, and the length of each cycle. Alternatively, one or more of these traction parameters may be set, for example, by the manufacturer during construction of operator control unit 500 or actuator system 600. In one embodiment, traction parameters are independently adjustable by user 12 before or during use according to particular needs. At appropriate times, operator control unit 500 communicates with actuator system 600 so that fluid may be supplied to lifting mechanisms 18 to cause lifting mechanisms 18 to extend, thereby pushing support belt 14 upward and support belt 16 downward. Because support belts 14, 16 are snugly wrapped around the user's body, this decompressive force is transferred to the user's body to relieve stress on the spine.

The amount of force generated by lifting mechanisms 18 may be controlled by operator control unit 500 or any other suitable control device. In one embodiment, pressure generated within lifting mechanisms 18 may offload approximately fifty percent of the body weight of user 12. Traction device 10 may also stabilize the torso, while still allowing flexibility. This stabilization may prevent additional compressive forces on the spine due to bending and lifting. Traction device 10 may be ambulatory, meaning that it is portable and wearable during everyday activities. Thus, in one embodiment, device 10 may be applied at home, at work, at play, or during travel at the convenience of user 12. Therefore, user 12 may be more likely to comply with therapy guidelines than if user 12 was required to travel to a clinic for therapy.

Figure 2A:
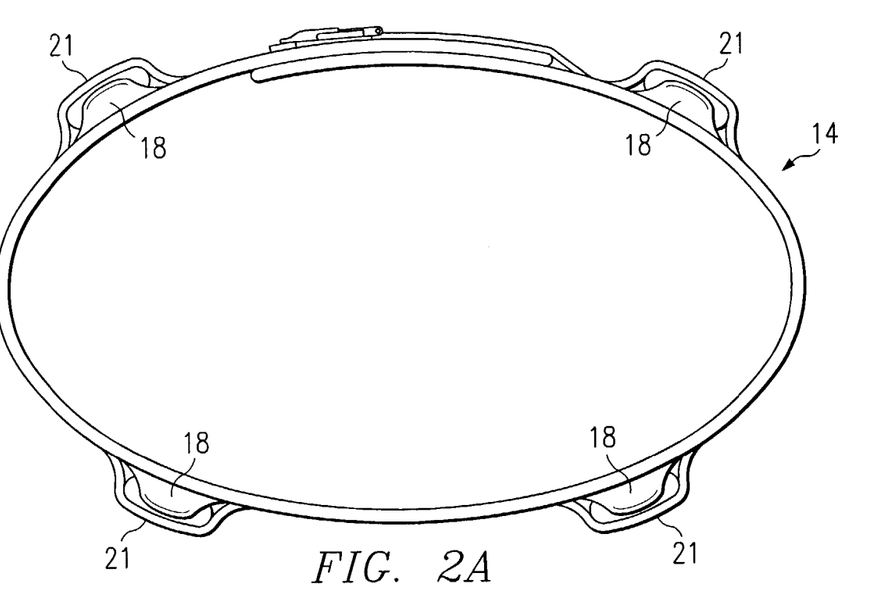
FIGS. 2A and 2B illustrate example locations for lifting mechanisms associated with an ambulatory cyclic traction device.
Figure 2B:
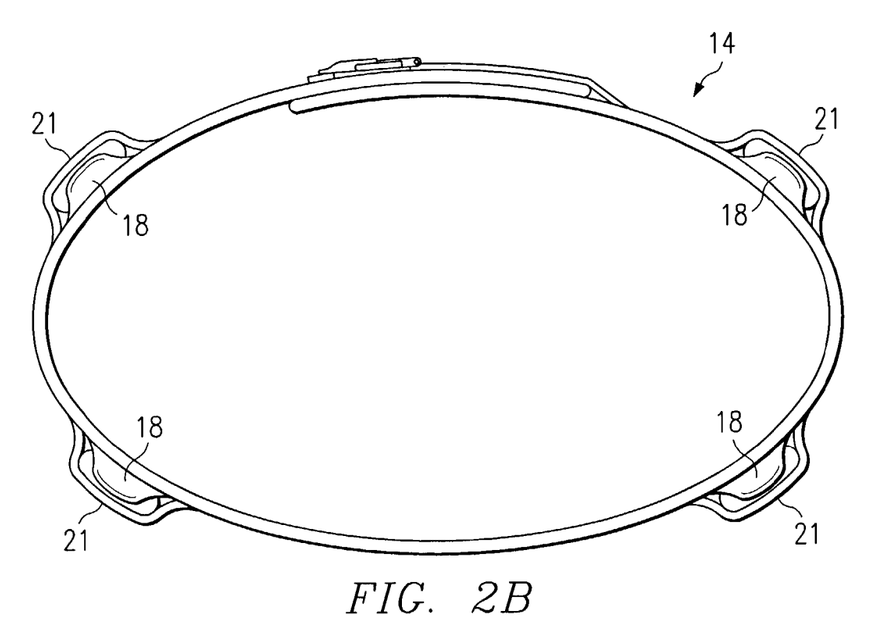

FIGS. 2A and 2B illustrate example locations for lifting mechanisms 18. FIG. 2A illustrates example locations for lifting mechanisms 18 for normal spinal decompression. As illustrated, four lifting mechanisms 18 may be used, with two located near the back of user 12 and two located towards the front of user 12. This configuration allows for application of a decompressive force to the spine, yet still allows user 12 to perform daily operations without undue hindrance. FIG. 2B illustrates a different configuration that also restricts motion of user 12 from side-to-side, in addition to placing the spine of user 12 into traction. This may be particularly useful for treating scoliosis. By locating lifting mechanisms 18 towards the side of user 12, side-to-side motion may be restricted and a straightening force may be applied to the spine to treat the spinal curvature effects of scoliosis. Although four lifting mechanisms 18 are illustrated in FIGS. 2A and 2B, any suitable number of lifting mechanisms 18 may be used.

Figure 3:
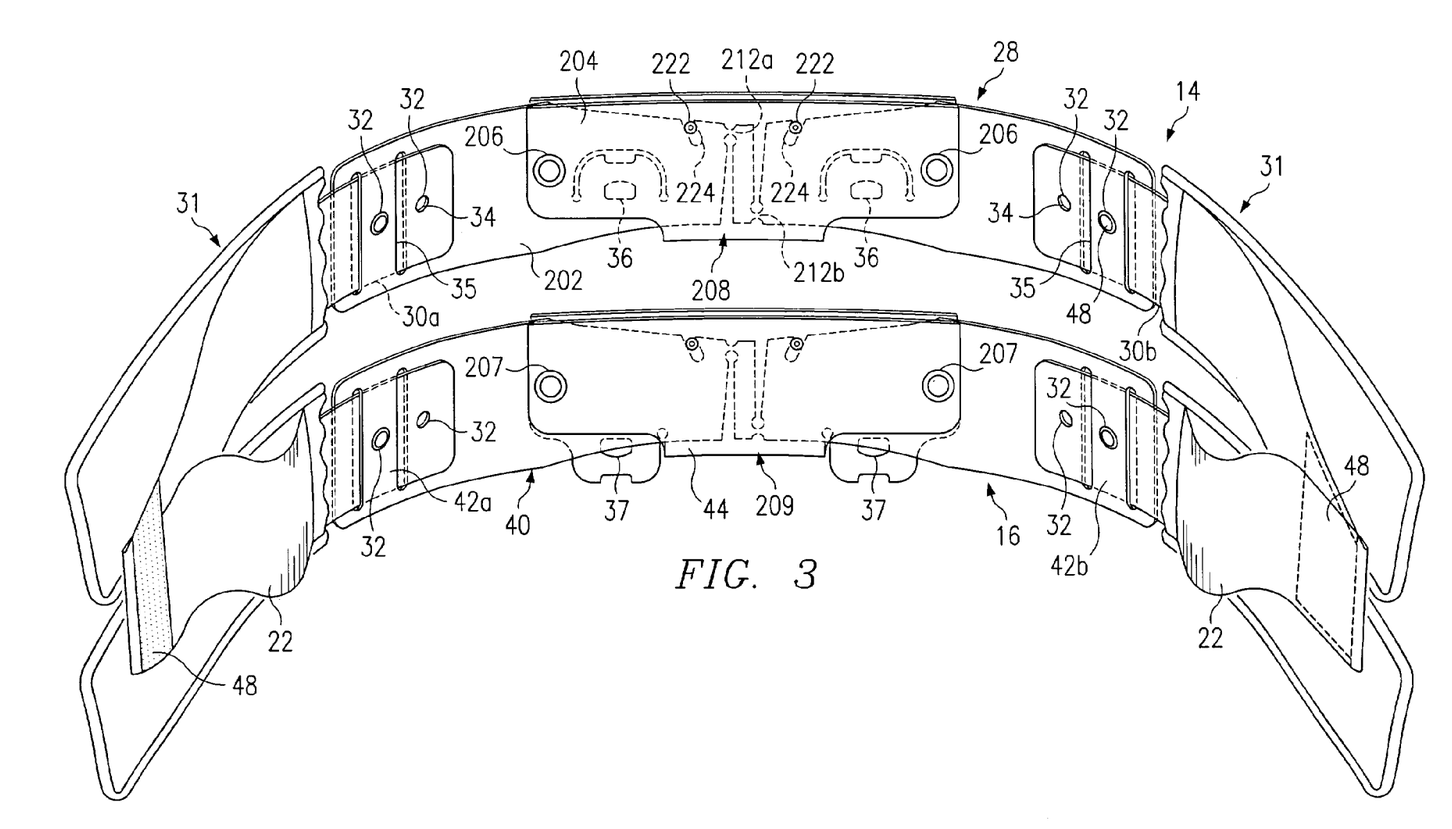
FIG. 3 illustrates example upper and lower support belts of an ambulatory cyclic traction device.

FIG. 3 illustrates an example traction device 10 showing additional details of support belts 14, 16. In one embodiment, support belt 14 is formed from a back belt 28 and a pair of front belts 30a, 30b. Back belt 28 and front belts 30a, 30b are generally rigid in the direction of support (up and down in this example) and may be formed from plastic or other suitable material. Front belts 30a, 30b are each formed with a number of holes 32 and back belt 28 is formed with a number of holes 34 to allow selective adjustment of the size of support belt 14. Back belt 28 may include one or more slits 35 near each end to help secure and allow for adjustment of front belts 30a, 30b with respect to back belt 28. Front belts 30a, 30b and back belt 28 may be coupled together using a rivet or other suitable connector placed through a desired hole 32 in back belt 28 and a desired hole 34 in front belts 30a, 30b (not explicitly shown in FIG. 3).

Back belt 28 is positioned between two plates 204. The plate 204 that is positioned to the exterior of back belt 28 is formed with notches 36 that couple to portions of lifting mechanisms 18 and facilitate transferring of a decompressive force from lifting mechanisms 18 to back belt 28. Similar notches exist in front belts 30a, 30b for facilitating transferring of a decompressive force from lifting mechanisms 18 to front belts 30a, 30b, but these are hidden in the example of FIG. 3 by an outer sleeve 31. Plates 204 are generally rigid in the direction of support and, as such, may be formed from plastic or any other suitable material that allows for transferring of forces from lifting mechanisms 18 to back belt 28. In one embodiment, back belt 28 is coupled to plates 204 at two pivots 206. Any appropriate component may be used to couple back belt 28 to plates 204 at pivots 206 so as to allow back belt 28 to rotate relative to plates 204 at pivots 206. Pivots 206, along with a canting mechanism 208 incorporated in back belt 28, allow back belt 28 to move in relation to plates 204 to conform to the underlying bone structure and natural generally conical shape of the user's torso below the ribs to assist in proper fitting of support belt 14 to user 12, as described more fully below.

An outer sleeve 31 preferably encases front belts 30a, 30b and back belt 28. Portions of outer sleeve 31 are cut away in FIG. 3 for clarity. Outer sleeve 31 may be formed from fabric or other suitable material and may be formed in a number of sections to facilitate access to back belt 28 and front belts 30a, 30b for adjustment. Outer sleeve 31 preferably provides an attractive look to support belt 14 and may provide cushioning comfort to user 12 with appropriate padding. Outer sleeve 31 may also cover up conduits 602 and/or any wires connecting operator control unit 500 and actuator system 600.

Support belt 16 is similar to support belt 14. Support belt 16 includes a back belt 40 and a pair of front belts 42a, 42b. Back belt 40 and front belts 42a, 42b are substantially similar to back belt 28 and front belts 30a, 30b, respectively, and include a pair of plates 44. The plate 44 that is positioned to the exterior of back belt 40 is formed with notches 37 facing downward rather than upward to allow transference of forces from lifting mechanisms 18 in a downward direction. In one embodiment, back belt 40 is coupled to plates 44 at two pivots 207. Any appropriate component may be used to couple back belt 40 to plates 44 at pivots 207 so as to allow back belt 40 to rotate relative to plates 44 at pivots 207. Pivots 207, along with a canting mechanism 209 incorporated in back belt 40, allow back belt 40 to move in relation to plates 44 to conform to the underlying bone structure and natural generally conical shape of the user's torso above the hips to assist in proper fitting of support belt 16 to user 12, as described more fully below.

Also shown more clearly in FIG. 3 is common strap 22. Common strap 22 connects to both support belts 14, 16, thereby allowing substantially equivalent and substantially simultaneous adjustment of support belts 14, 16 about the body of user 12. In this example, hook and loop type fasteners 48, commonly known as VELCRO, are disposed on common strap 22 to secure common strap 22 into place about the user's body.

As described above, back belts 28, 40 include canting mechanisms 208, 209. Since canting mechanisms 208 and 209 are similar, for brevity only canting mechanism 208 is described in detail. Canting mechanism 208 is typically positioned adjacent the back of user 12 when traction device 10 is worn by user 12. When worn in such a manner, pivots 206 and a pair of hinges 212a, 212b of canting mechanism 208 allow back belt 28 to conform to the contours of user's 12 body, and particularly to the torso below the ribs having a natural generally conical shape (opening upward for upper support belt 14). Therefore, canting mechanism 208 may be used to more closely fit support belt 14 to users 12 having a variety of different sizes and shapes, while maintaining substantial symmetry, to provide more effective treatment.

Canting mechanism 208 may be integrally formed with back belt 28. For example, back belt 28 and canting mechanism 208 may be formed from a single piece of plastic and hinges 212a, 212b may be formed by molding or cutting this piece of plastic into the desired shape. Alternatively, any other suitable method of fabricating these components from any appropriate material may be used. Hinges 212a, 212b may be formed by forming or cutting slots in back belt 28. The term "slots" is meant to include both slits and wedges formed in back belt 28. If slits are formed, the slits may be pulled open to create wedges when back belt 28 is coupled to plates 204. Furthermore, a circular or other cut-out may be formed at the ends of the slots to aid in opening of the slots and reduce the resultant stresses on hinges 212a, 212b. Hinges 212a, 212b may be referred to collectively as a polycentric hinge.

Depending upon which part of the user's body that back belt 28 is to be positioned around, one or more limitors 222 may be used to limit the movement of back belt 28 in a certain direction. Limitor slots 224 may be formed in back belt 28 and may be configured and positioned such that when back belt 28 is moved downward, limitor slots 224 engage with limitors 222 on a plate 204 and prevent further downward movement of back belt 28 with respect to plate 204. In this case, limitors 222 may be peg-like extensions from plate 204 on the side of plate 204 to which back belt 28 is attached, extending toward the other plate 204. Although limiting the downward movement of back belt 28 is described, limitors 222 and limitor slots 224 may be positioned in other embodiments so as to limit the upward movement of back belt 28, instead of or in addition to limiting downward movement.

Figure 4:
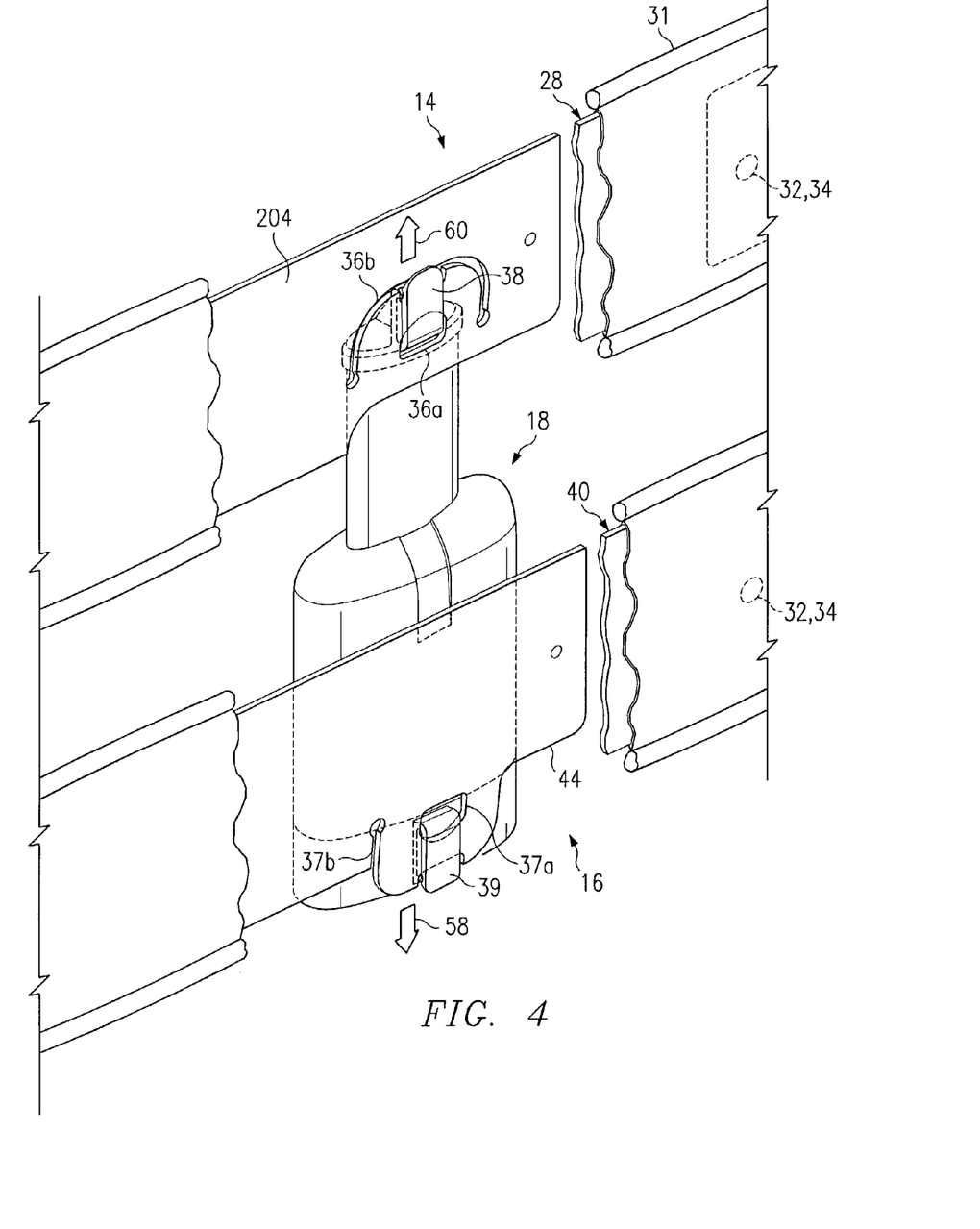
FIG. 4 illustrates an example lifting mechanism of an ambulatory cyclic traction device.

FIG. 4 illustrates support belts 14, 16 with portions cut away to illustrate the coupling of lifting mechanisms 18 between support belts 14, 16. For brevity, the coupling of only one lifting mechanism 18 is illustrated and described in detail. In the illustrated embodiment, rear plate 204 includes a notch 36a and rear plate 44 includes a notch 37a. Similar notches may be formed in front belts 30a, 30b, 42a, 42b for other lifting mechanisms 18. Lifting mechanism 18 is coupled between support belts 14, 16 by engaging notch 36a with a clip 38 and notch 37a with a clip 39 as shown, which in one embodiment may be accomplished very quickly during construction of traction device 10 and does not require any additional fasteners. Access to notches 36 and 37 may be provided through pouches 21 and 19. Other suitable methods may be used to couple lifting mechanisms 18 between support belts 14, 16.

In one embodiment, notches 36a and 37a are rounded on their upper and lower surfaces, respectively (as illustrated by the hidden lines), to allow corresponding clips 38 and 39, respectively, of lifting mechanism 18 to rotate side-to-side within notches 36a and 37a, in the general plane of support belts 14, 16, as user 12 moves. In addition, notches 36b and 37b may be provided to allow clips 38 and 39, respectively, of lifting mechanism 18 to rotate forward and back, into and out of the general plane of support belts 14, 16 as user 12 moves. These features, singly or in combination, may provide increased comfort, wearability, and effectiveness. In addition, permitting such rotation of lifting mechanism 18 may help ensure that the forces applied through lifting mechanism to support belts 14, 16 remain substantially along the vertical axis of lifting mechanism 18, which may not only increase effectiveness but may also help prevent lifting mechanism 18 or a portion thereof, such as an internal seal, from failing due to deformation of lifting mechanism 18.

In operation, in order to apply a decompressive force between support belts 14, 16, lifting mechanism 18 is pressurized causing a downward force on the lower end of lifting mechanism 18, as denoted by arrow 58, and an upward force on the upper end of lifting mechanism 18, as denoted by arrow 60. This in turn generates forces in support belts 14, 16 in opposite directions, thereby resulting in traction of the spine of user 12. Additional details of an example lifting mechanism 18 are described below with reference to FIGS. 5A through 5D.

Figure 5A:
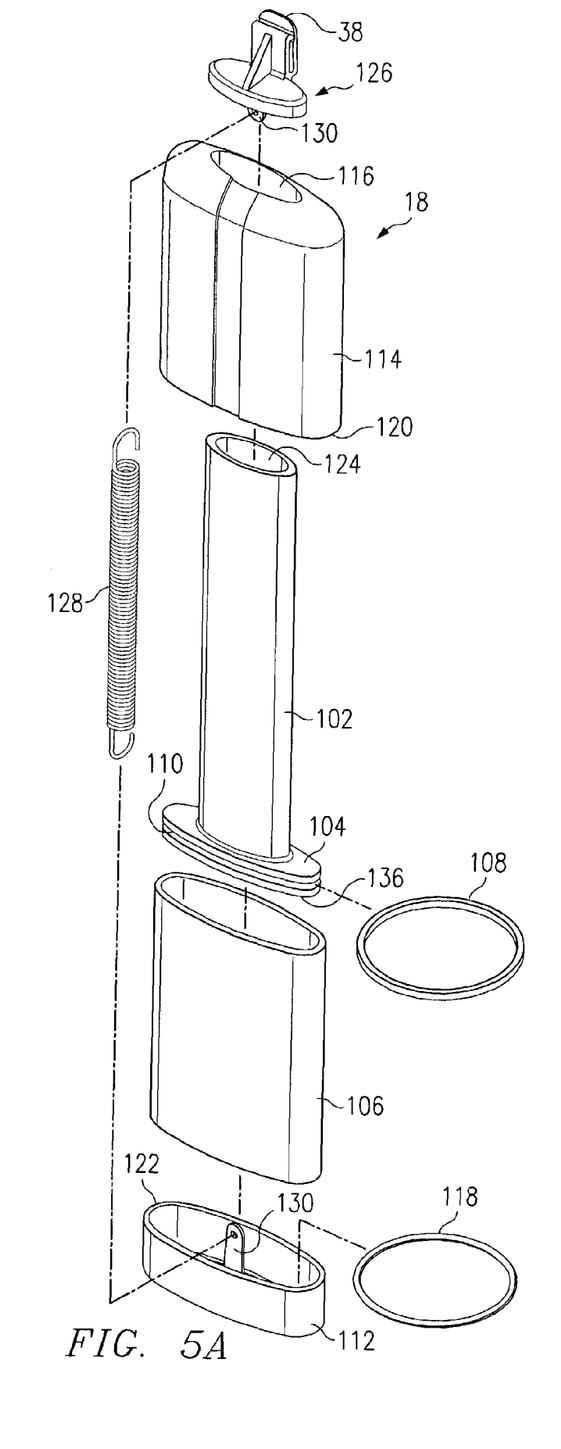
FIGS. 5A through 5D further illustrate an example lifting mechanism of an ambulatory cyclic traction device.
Figure 5B:
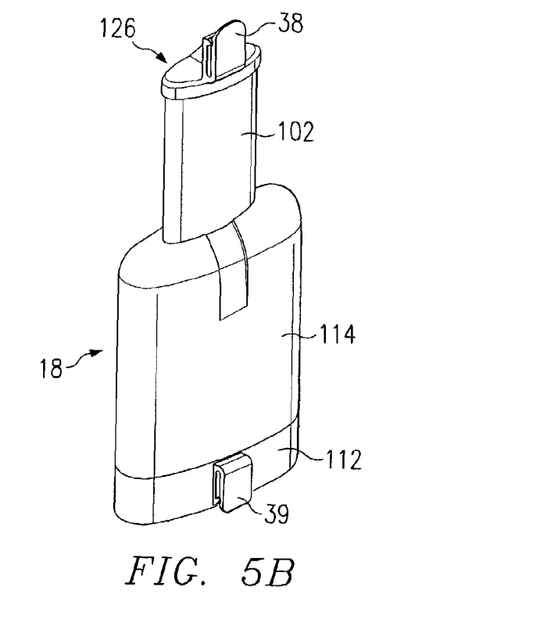
Figure 5C:
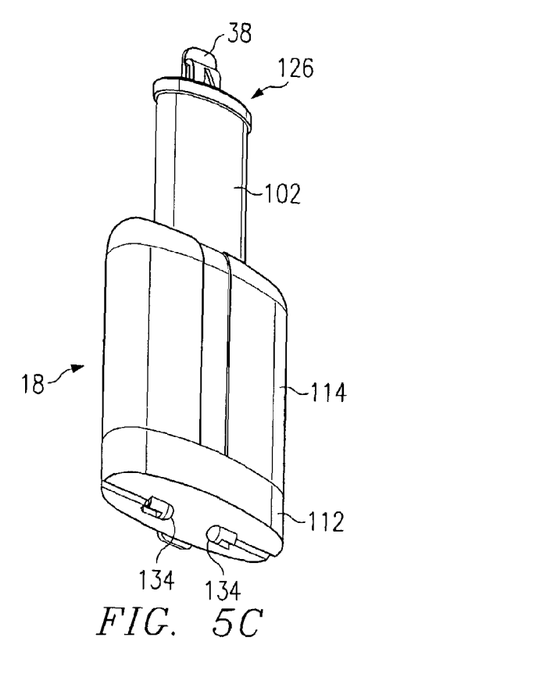
Figure 5D:
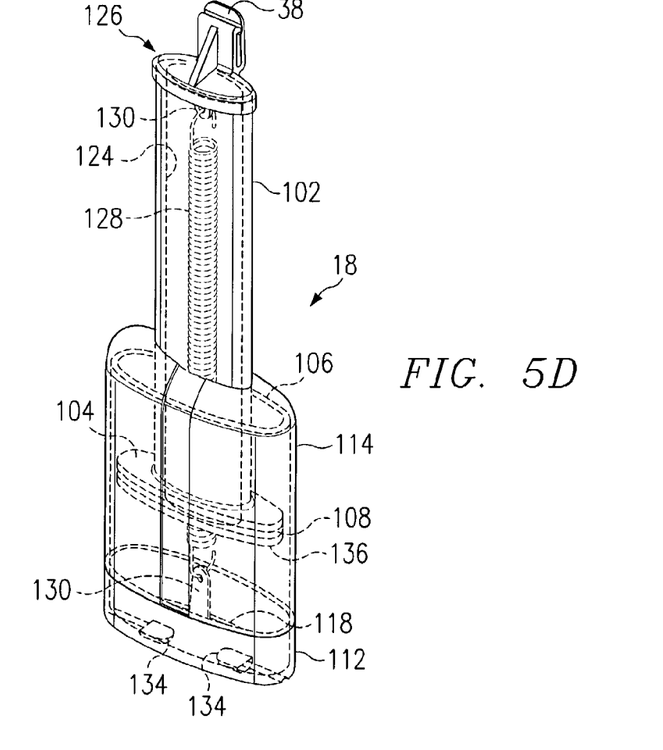

FIGS. 5A through 5D illustrate an example lifting mechanism 18 of traction device 10. FIG. 5A is an exploded view of lifting mechanism 18, FIGS. 5B and 5C are perspective views of an assembled lifting mechanism 18, and FIG. 5D is another perspective view of lifting mechanism 18 illustrating internal components of lifting mechanism 18 using hidden lines.

In one embodiment, example lifting mechanism 18 has a substantially elliptical cross-section. The term "elliptical" is meant to include all non-circular ellipses, ovals, "egg" shapes, "bean" shapes, and any other similar shapes. When lifting mechanism 18 is positioned as a part of traction device 10, this substantially elliptical cross-section provides greater comfort to the user and has a lower profile against the body of user 12 than would a similar lifting mechanism having a cylindrical cross-section. Furthermore, other shapes that conform to user 12 may also be used. However, as described below, the use of such a substantially elliptical or other non-circular cross-sections may present problems that are not associated with a cylindrical cross-section.

In one embodiment, lifting mechanism 18 includes a piston having a piston rod 102 and a flange 104 that is inserted into a sleeve 106. Piston rod 102, flange 104, and sleeve 106 may each have a substantially elliptical cross-section. However, any other appropriate shape may be used for one or more of these components. For example, flange 104 and sleeve 106 may have substantially elliptical cross-sections and piston rod 102 may have a circular or other appropriate cross-section. Flange 104 is configured such that it conforms to the inside of sleeve 106 and may slide inside sleeve 106. A piston ring 108 may be positioned around a perimeter of flange 104 to form a seal between flange 104 and sleeve 106. A groove 110 may be formed around the perimeter of flange 104 to provide a seating for piston ring 108. Piston ring 108 may be fabricated from rubber or any other appropriate material.

Since sleeve 106 has a non-circular cross-section, if the interior of sleeve 106 is pressurized to effect the movement of piston rod 102 (as described more fully below), stresses are developed in sleeve 106 and give sleeve 106 the tendency to deform into a cylindrical shape. This is undesirable since it may induce leakage between sleeve 106 and piston ring 108. Therefore, sleeve 106 may be fabricated from a metal, such as aluminum, or another appropriate material to withstand these stresses and prevent such deformation. In the example embodiment, sleeve 106 has openings at either end and thus does not form an airtight chamber into which air or any other appropriate fluid may be inserted to move piston rod 102. Therefore, to form an airtight chamber, a housing is formed around sleeve 106.

The housing includes a housing bottom 112 which fits over one end of sleeve 106 and a housing top 114 which fits over the other end of sleeve 106 and contacts housing bottom 112. Housing top 114 also provides an opening 116 through which piston rod 102 may be extended. A housing ring 118 may be inserted into housing bottom 112 to provide a seal between sleeve 106 and housing bottom 112 to prevent or reduce the leakage of air or other fluids from sleeve 106. A lower edge 120 of housing top 114 may be sonically welded to an upper edge 122 of housing bottom 112, although housing bottom 112 and housing top 114 may be coupled in any other appropriate manner to form a substantially airtight enclosure. In one embodiment, sleeve 106 is forced into a sealing relationship with housing ring 118 when housing top 114 is welded or otherwise coupled to housing bottom 112. Housing bottom 112 and housing top 114 may be fabricated from plastic or any other suitable material. Furthermore, housing top 114 may be eliminated in certain embodiments and sleeve 106 may have a partially enclosed first end and be bonded with housing bottom 112 at a second end. However, housing top 114 may be used when bonding between sleeve 106 and housing bottom 112 is infeasible due to the use of differing materials to fabricate sleeve 106 and housing bottom 112.

In one embodiment, piston rod 102 may be hollow such that a cavity 124 extends from one end of piston rod 102 to the other. Cavity 124 extends through flange 104 such that air or another fluid in sleeve 106 may travel through piston rod 102 in cavity 124. Therefore, a piston rod top 126 is coupled to the end of piston rod 102 opposite flange 104 to prevent this air or other fluid from escaping from sleeve 106 through piston rod 102. Piston rod top 126 may be sonically welded to piston rod 102 or coupled to piston rod using any other suitable technique. As with piston rod 102, piston rod top 126 may be fabricated from plastic or any other appropriate material.

Cavity 124 is provided in one embodiment so that a spring 128 or other appropriate elastic member may be used to connect housing bottom 112 and piston rod top 126. Spring 128 is used to provide a force to retract piston rod 102 into sleeve 106 when a sufficient air or other fluid pressure does not exist in sleeve 106 to counteract the retraction force generated by spring 128, such as when traction device 10 is not in use. In one embodiment, providing a retracting spring 128 within cavity 124 of piston rod 102 allows the total height of lifting mechanism 18 to be minimized, for the same amount of maximum extension of lifting mechanism 18, relative to a lifting mechanism in which a compressed spring is used to return piston rod 102 into sleeve 106. This may provide an advantage in terms of comfort, wearability, aesthetics, and effectiveness. Housing bottom 112 and piston rod top 126 may each include a hook point 130, which may be used to attach spring 128 to housing bottom 112 and piston rod top 126. Alternatively, any other appropriate attachment points located in any other suitable positions may be used. Housing bottom 112 and piston rod top 126 may also include clips 38, 39 for coupling lifting mechanism 18 to support belts 14, 16, as described above.

As shown in FIG. 5C, housing bottom 112 includes one or more inlets 134 through which air or any other appropriate fluid may be pumped into and out of sleeve 106. For example, inlets 134 may be configured such that conduits 602 from actuator system 600 may be coupled to inlets 134. Using such a system, a fluid may be pumped into sleeve 106 until a sufficient amount of pressure is exerted against a bottom face 136 of flange 104 (shown in FIG. 5A) to cause flange 104 to move away from housing bottom 112 and thus for piston rod 102 to extend further from housing top 114. Air or any other appropriate fluid may be pumped into sleeve 106 through inlets 134 until piston rod 102 is in an appropriate position. As described above, multiple lifting mechanisms 18 may be coupled between support belts 14, 16, and the piston rod 102 of each lifting mechanism 18 may be extended such that appropriate spacing is maintained between support belts 14, 16 and an appropriate force is applied to place the spine or other joint in traction. Once this appropriate position and force are reached, the pressure against flange 104 may be maintained for a predetermined time interval to provide, over a series of such time intervals, cyclic traction to user 12 and reduce compressive forces on the spine or other joint. An example control system for controlling pressurization/depressurization of lifting mechanisms 18 for cyclic traction is described below with reference to FIGS. 6 and 7.

Figure 6:
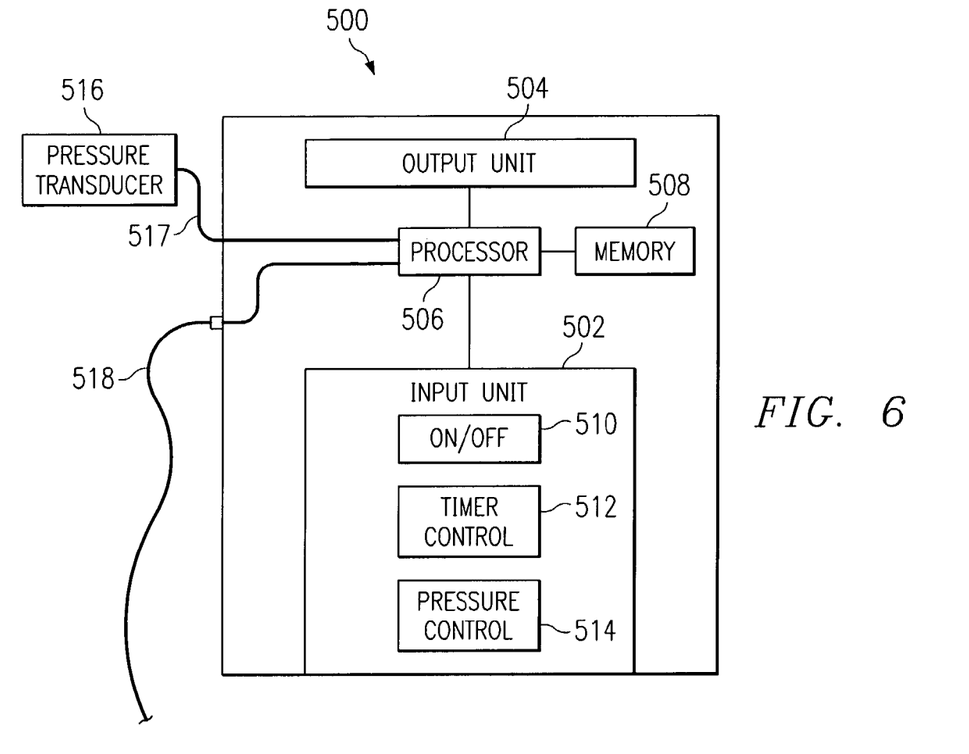
FIG. 6 illustrates an example operator control unit for an ambulatory cyclic traction device.

FIG. 6 illustrates an example operator control unit 500 for use with traction device 10. Operator control unit 500 includes an input unit 502, an output unit 504, a processor 506, and a memory 508.

Input unit 502 may include one or more dials, touch screens, keypads, or other suitable input devices to allow user 12 or another suitable person to input desired information into operator control unit 500. For example, as shown in FIG. 5, input unit 502 may include an on/off control 510, a timer control 512, and a pressure control 514. These elements and/or other elements associated with input unit 502 allow user 12 to control the pressurization of lifting mechanisms 18. For example, on/off control 510 may allow a user to turn operator control unit 500 on or off. Timer control 512 may allow user 12 to set the number of traction cycles, set a predetermined time interval for pressurization of lifting mechanisms 18 during a traction cycle, and otherwise control the cyclic nature of traction device 10. Pressure control 514 may allow user 12 to set a desired pressure level, set a desired pressure range about a user-specified, predetermined, or other pressure level, and otherwise control the amount of pressure inside lifting mechanisms 18, thereby controlling the amount of traction to a portion of the user's body. On/off control 510, timer control 512, and pressure control 514 may be either digital or analog devices. For example, timer control 512 may be a dial to control the time interval or a time may be entered using a keypad. Similarly, pressure control 514 may be a dial to control the pressure level or a pressure level may be entered using a keypad. Output unit 504 may include any suitable visual display unit.

Processor 506 may include any suitable processing unit that executes logic. One of the functions of processor 506 is to receive information from input unit 502 and use this information to control the electrical, electromechanical, and/or mechanical components of actuator system 600 for facilitating the pressurization of lifting mechanisms 18. For example, processor 506 may use any suitable software stored in memory 508 to control the components of actuator system 600. Processor 506 may also receive pressure data associated with lifting mechanisms 18 from one or more pressure transducers 516. As described in more detail below, processor 506 uses this pressure data to control the pressurization of lifting mechanisms 18 within predetermined pressure ranges.

Memory 508 may include files, stacks, databases, or any other suitable organizations of volatile or nonvolatile memory. Memory 508 may be RAM, ROM, CD-ROM, removable memory devices, or any other suitable memory devices that allow storage and/or retrieval of data. For example, memory 508 may store one or more software programs that are used by processor 506 to control the pressurization of lifting mechanisms 18. In addition, memory 508 may store historical information concerning operation of traction device 10.

Pressure transducer 516 may be any suitable transducer or component that can sense pressure inside lifting mechanism 18 and convey this information to processor 506 of operator control unit 500. Pressure transducers 516 may be coupled to processor 506 via one or more wires 517; however, the communication between pressure transducer 516 and processor 506 may be wireless. Similarly, operator control unit 500 may communicate with actuator system 600 via any suitable wire 518 or through any suitable wireless communication link.

Figure 7:
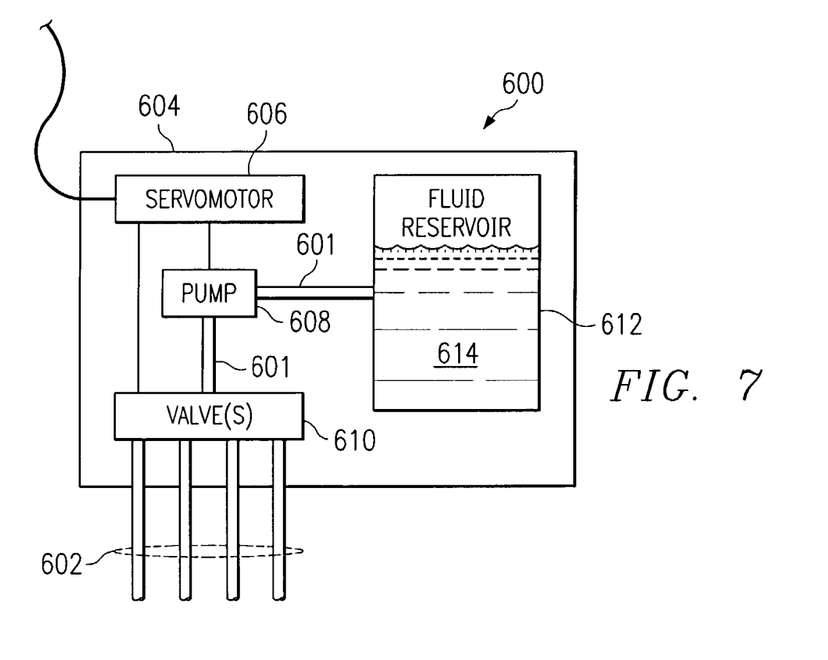
FIG. 7 illustrates an example actuator system for an ambulatory cyclic traction device.

FIG. 7 illustrates an example actuator system 600 for use with traction device 10. In the illustrated embodiment, actuator system 600 includes a housing 604 that houses a servomotor 606, a pump 608, one or more valves 610, a fluid reservoir 612 containing a fluid 614, and a plurality of conduits 601 and 602. Although not illustrated, one or more relief valves may be associated with actuator system 600 to prevent over-pressurization.

Housing 604 may be any suitable housing formed from any suitable material. Housing 602 may facilitate the attachment of actuator system 600 to lower support belt 16 via any suitable attachment system.

Servomotor 606 receives signals from processor 506 of operator control unit 500 and functions to control pump 608 and valves 610 to control the amount of pressurization of lifting mechanisms 18. Pump 608 may be any suitable pump operable to pump fluid 614 in fluid reservoir 612 through conduit 601, valves 610, and conduits 602 to lifting mechanisms 18. Valves 610 may be any suitable valves that control the amount of fluid 614 transferring to and from lifting mechanisms 18 through conduit 602. There may be one valve 610 that controls the amount of fluid going to each lifting mechanism 18 or there may be separate valves 610 for each lifting mechanism 18. In a particular embodiment, there is one valve 610 that controls the amount of fluid going to two lifting mechanisms 18 near the front of user 12 and one valve 610 that controls the amount of fluid going to two lifting mechanisms 18 near the rear of user 12.

Fluid reservoir 612 may be any suitable container that is operable to house fluid 614. Fluid 614 may be any suitable fluid, such as hydraulic fluid, water, or a suitable gas such as air. Conduits 601 and 602 are any suitable tubes and/or pipes that are operable to allow fluid to flow therein. In one embodiment, conduits 601 and 602 are flexible hoses that may be wrapped around the user's body and attached to lifting mechanisms 18 via inlets 134. Any suitable connectors may be used to connect conduits 601 and 602 to various components such as fluid reservoir 612, pump 608, valve 610, and lifting mechanisms 18.

In operation of one embodiment of the invention, user 12 turns on operator control unit 500 by activating on/off control 510. User 12 may input a desired pressure level, a desired pressure range about a user-specified, predetermined, or other pressure level, or both using pressure control 514. User 12 may input a number of cycles, a cycle time, or both using timer control 512. Using a suitable software program stored in memory 508, processor 506 then instructs servomotor 606 of actuator system 600 to activate pump 608 and start pumping fluid 614 through conduit 601, valve 610, and conduit 602 to lifting mechanisms 18 according to the input information. In this embodiment, assume that one valve 610 controls the amount of fluid going to two lifting mechanisms 18 near the front of user 12 and one valve 610 controls the amount of fluid going to two lifting mechanisms 18 near the rear of user 12. The fluid delivered to lifting mechanisms 18 causes lifting mechanisms 18 to fill with fluid until the desired pressure, and thus the desired decompressive force, is obtained. As described below, the pressure in lifting mechanism 18 may be maintained within a range about a user-specified, predetermined, or other pressure level for a user-specified, predetermined, or other time interval by utilizing pressure transducers 516 associated with each lifting mechanism 18. After the traction cycle is completed, processor 506 then instructs servomotor to activate pump 608 and valves 610 to start drawing fluid 614 from lifting mechanisms 18 back through conduit 602, valves 610, conduit 601, and into fluid reservoir 612. Lifting mechanisms 18 are then retracted to their normal positions before the next cycle begins, as described above.

If, for example, user 12 bends forward, then the pressure in the lifting mechanisms 18 near the front of user 12 will increase and the pressure in the lifting mechanisms 18 near the rear of user 12 will decrease. In this case, pressure transducers 516 coupled to the front lifting mechanisms 18 will detect the increase and communicate this to processor 506. Pressure transducers 516 coupled to the rear lifting mechanisms 18 will detect the decrease and communicate this to processor 506. If the pressure in the front lifting mechanisms 18 increases above an upper threshold, the pressure in the rear lifting mechanisms 18 decreases below a lower threshold, or both, then processor 506 may instruct servomotor 606 and pump 608 to bleed fluid 614 out of, withdraw fluid 614 from, or otherwise reduce the fluid pressure within the front lifting mechanisms 18 and to pump more fluid 614 into the rear lifting mechanisms 18 to maintain the desired pressurization in all lifting mechanisms 18. Similarly, if, for example, user 12 bends backward, then the pressure in the lifting mechanisms 18 near the front of user 12 will decrease and the pressure in the lifting mechanisms 18 near the rear of user 12 will increase. In this case, pressure transducers 516 coupled to the front lifting mechanisms 18 will detect the decrease and communicate this to processor 506. Pressure transducers 516 coupled to the rear lifting mechanisms 18 will detect the increase and communicate this to processor 506. If the pressure in the front lifting mechanisms 18 decreases below a lower threshold, the pressure in the rear lifting mechanisms 18 increases above an upper threshold, or both, then processor 506 may instruct servomotor 606 and pump 608 to bleed fluid 614 out of, withdraw fluid 614 from, or otherwise reduce the fluid pressure within the rear lifting mechanisms 18 and to pump more fluid 614 into the front lifting mechanisms 18 to maintain the desired pressurization in all lifting mechanisms 18. One example of a traction or pressurization/depressurization cycle is described below with reference to FIG. 8.

Figure 8:
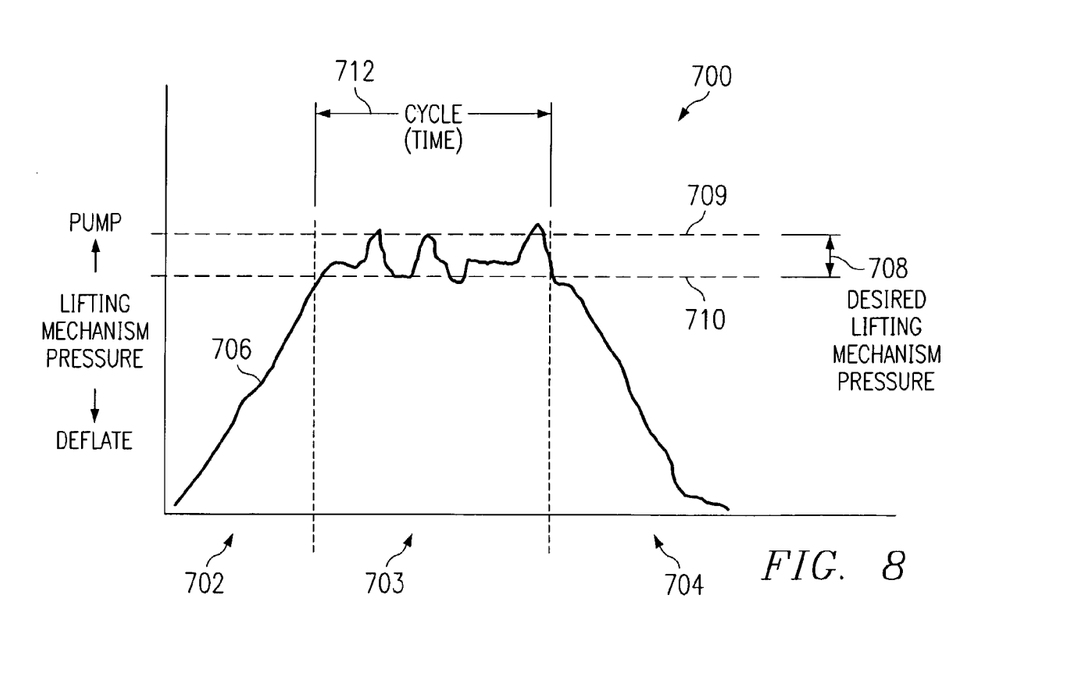
FIG. 8 illustrates an example traction or pressurization/depressurization cycle for an ambulatory cyclic traction device.

FIG. 8 illustrates one full example traction cycle for lifting mechanism 18 according to the teachings of the present invention. One traction cycle includes a pressurization period 702, a pressure maintenance period 703, and a depressurization period 704. A typical pressurization profile is represented by curve 706. During pressurization period 702, pressure in lifting mechanism 18 (and hence traction of a portion of users 12 body) increases to fall generally within the band 708 defined by dotted lines 709 and 710. Band 708 includes a pressure range about a desired lifting mechanism pressure level, which corresponds with a desired traction of a portion of the user's body. This pressure is maintained within band 708 for a predetermined time interval during pressure maintenance period 703, as denoted by reference numeral 712. As illustrated by curve 706, there may be some small amount of over-pressurization and under-pressurization during time interval 712 depending on, for example, motion of user 12. However, suitable hysteresis may be built in to avoid rapid pressurization and depressurization of lifting mechanisms 18 during time interval 712. Lifting mechanism 18 pressure is maintained within band 708 with the use of pressure transducers 516 that are associated with one or more lifting mechanism 18. A typical time interval 712 is sixty seconds; however, other suitable time intervals may be utilized. After a predetermined time interval 712 is completed, then fluid begins to be released from lifting mechanisms 18, as denoted by the decrease in curve 706 during depressurization period 704. As described above, any suitable number of cycles may be performed, according to particular needs. In one embodiment, a predetermined time interval 712 is adjusted via timer 512 to an infinite (or equivalent) time period, which results in traction device 10 being used as a brace providing continuous support to user 12.

Although the present invention is described with several embodiments, numerous changes, substitutions, variations, alterations, and modifications may be suggested to one skilled in the art. It is intended that the invention encompass all such changes, substitutions, variations, alterations, and modifications as fall within the spirit and scope of the appended claims.

What is claimed is:

1. A method for treating a portion of a user's body, comprising:

positioning two support belts about the user's body, the support belts each having a front portion corresponding to a front portion of the user's body and a back portion corresponding to a back portion of the user's body, the support belts further having one or more fluidic lifting mechanisms having end portions coupled to generally the front portions of the support belts and one or more fluidic lifting mechanisms having end portions coupled to generally the back portions of the support belts, the one or more lifting mechanisms adapted to apply a decompressive force to the portion of the user's body through the support belt when the support belts are positioned about the user's body;

using a control system coupled to the one or more lifting mechanisms to supply fluid to and pressurize the one or more lifting mechanisms to cause the one or more lifting mechanisms to cyclically apply the decompressive force to the portion of the user's body through the support belts when the support belts are positioned about the user's body such that the decompressive force is applied for a predetermined time interval during each of a series of traction cycles, whereby mobility of the portion of the user's body is restricted during each of the series of traction cycles; and maintaining a pressure in each lifting mechanism during each traction cycle within a predetermined pressure range defined by a lower threshold and an upper threshold, the control system including a pressure transducer for monitoring pressure within the lifting mechanisms, and the control system supplying additional fluid to the lifting mechanism in response to the pressure in the lifting mechanism falling below the lower threshold, the control system reducing fluid pressure in the lifting mechanism in response to the pressure in the lifting mechanism rising above the upper threshold.

2. The method of claim 1, wherein the portion of the user's body comprises a portion of the user's spine.

3. The method of claim 1, wherein the predetermined time interval is a user-specified desired time interval.

4. The method of claim 1, wherein the number of traction cycles in the series is user-specified.

5. The method of claim 1, wherein the predetermined pressure range is a user-specified desired pressure range, defined about a user-specified desired pressure level.

6. The method of claim 5, wherein the user-specified desired pressure level is adjustable during use of the device.

7. The method of claim 1, wherein the control system comprises a pump operable to supply the fluid and one or more valves operable to control the amount of fluid supplied to the one or more fluidic lifting mechanisms.

8. The method of claim 7, wherein a plurality of lifting mechanisms are coupled in series to the valve.

9. The method of claim 7, wherein:
the one or more lifting mechanisms comprise four lifting mechanisms; and
the control system comprises a first valve for controlling the amount of fluid supplied to a first set of two lifting mechanisms and a second valve for controlling the amount of fluid supplied to a second set of two lifting mechanisms.

10. The method of claim 1, wherein the control system comprises a pressure control coupled to a processor, the pressure control and the processor operating in conjunction with one another to control a pressure m the lifting mechanism.

11. The method of claim 10, wherein the control system further comprises a timer, the timer and the processor operating in conjunction with one another to maintain the pressure in the lifting mechanism within the predetermined pressure range for the predetermined time interval associated with a traction cycle.

12. The method of claim 1, further comprising using a common adjustment strap coupled to each of the support belts to substantially simultaneously adjust the support belts in substantially the same amount about the user's body.

13. The method of claim 1, further comprising using a canting mechanism coupling opposing portions of a support belt to allow the opposing portions to rotate about associated pivots to allow the support belt to conform to the user's body and to synchronize the movement of the opposing portions of the support belt such that movement of one portion upward or downward requires movement of the other portion upward or downward in a substantially equivalent amount.

14. An ambulatory cyclic traction device, comprising:
two support belts configured to be positioned about a user's body, the support belts each having a front portion corresponding to a front portion of the user's body and a back portion corresponding to a back portion of the user's body;
one or more fluidic lifting mechanisms having end portions coupled to generally the front portions of the support belts and one or more fluidic lifting mechanisms having end portions coupled to generally the back portions of the support belts, the one or more front lifting mechanisms and the one or more back lifting mechanisms adapted to apply a decompressive force to a portion of the user's body between the support belts; and
a control system coupled to the one or more lifting mechanisms and operable to supply a fluid to the one or more lifting mechanisms to pressurize each lifting mechanism to cause the lifting mechanism to cyclically apply the decompressive force to the portion of the user's body through the support belts when the support belts are positioned about the user's body, such that the decompressive force is applied for a predetermined time interval during each of a series of traction cycles, whereby mobility of the portion of the user's body is restricted during each of the series of traction cycles;
wherein the control system includes a pressure transducer for monitoring pressure within the one or more lifting mechanisms, and wherein the control system is operable to maintain a pressure in each lifting mechanism during each traction cycle within a predetermined pressure range defined by a lower threshold and an upper threshold, the control system operable to supply additional fluid to the lifting mechanism in response to the pressure in the lifting mechanism falling below the lower threshold, the control system operable to reduce fluid pressure in the lifting mechanism in response to the pressure in the lifting mechanism rising above the upper threshold.

15. The device of claim 14, wherein the portion of the user's body comprises a portion of the user's spine.

16. The device of claim 14, wherein the predetermined time interval is a user-specified desired time interval.

17. The device of claim 14, wherein the number of traction cycles in the series is user-specified.

18. The device of claim 14, wherein the predetermined pressure range is a user-specified desired pressure range, defined about a user-specified desired pressure level.

19. The device of claim 18, wherein the user-specified desired pressure level is adjustable during use of the device.

20. The device of claim 14, wherein the control system comprises a pump operable to supply the fluid and one or more valves operable to control the amount of fluid supplied to the one or more fluidic lifting mechanisms.

21. The device of claim 20, wherein a plurality of lifting mechanisms are coupled in series to the valve.

22. The device of claim 20, wherein:
the one or more lifting mechanisms comprise four lifting mechanisms; and
the control system comprises a first valve for controlling the amount of fluid supplied to a first set of two lifting mechanisms and a second valve for controlling the amount of fluid supplied to a second set of two lifting mechanisms.

23. The device of claim 14, wherein the control system comprises a pressure control coupled to a processor, the pressure control and the processor operable to work in conjunction with one another to control a pressure in the lifting mechanism.

24. The device of claim 23, wherein the control system further comprises a timer, the timer and the processor operable to work in conjunction with one another to maintain the pressure in the lifting mechanism within the predetermined pressure range for the predetermined time interval associated with a traction cycle.

25. The device of claim 14, further comprising a common adjustment strap coupled to each of the support belts and operable to substantially simultaneously adjust the support belts in substantially the same amount about the user's body.

26. The device of claim 14, wherein at least one support belt comprises a canting mechanism coupling opposing portions of the support belt and operable to allow the opposing portions to rotate about associated pivots to allow the support belt to conform to the user's body and to synchronize the movement of the opposing portions of the support belt such that movement of one portion upward or downward requires movement of the other portion upward or downward in a substantially equivalent amount.

27. An ambulatory traction device, comprising:
two support belts configured to be positioned about a user's body, the support belts each having a front portion corresponding to a front portion of the user's body and a back portion corresponding to a back portion of the user's body;
one or more fluidic lifting mechanisms having end portions coupled to generally the front portions of the support belts and one or more fluidic lifting mechanisms having end portions coupled to generally the back portions of the support belts, the one or more front lifting mechanisms and the one or more back lifting mechanisms adapted to apply a decompressive force to a portion of the user's body through the support belts when the support belts are positioned about the user's body; and
a control system coupled to the lifting mechanisms and operable to cause the lifting mechanisms to cyclically apply the decompressive force to the portion of the user's body through the support belts when the support belts are positioned about the user's body, such that the decompressive force is applied for a predetermined time interval during each of a series of traction cycles, whereby mobility of the portion of the user's body is restricted during each of the series of traction cycles, the control system comprising:
a pump operable to supply a fluid through one or more conduits to the lifting mechanisms;
a valve associated with the conduits and operable to control the amount of fluid supplied through the conduits to the lifting mechanisms;
a pressure control operable to set a desired pressure level in the lifting mechanisms;
a timer operable to set the predetermined time interval;
a pressure transducer for monitoring pressure within the one or more lifting mechanisms; and
a processor associated with the pump, valve, pressure control, timer, and pressure transducer, the processor operable to receive pressure data from the pressure transducer and control the pump and the valve in response to input from the pressure control, timer and pressure transducer to maintain a pressure in the lifting mechanisms during each traction cycle within a predetermined pressure range about the desired pressure level.

28. The device of claim 27, wherein the control system further comprises a memory coupled to the processor, the memory operable to store historical information concerning operation of the device.

29. The device of claim 27, wherein:
each support belt comprises a pair of front belts coupled to a back belt; and
the device further comprises a common adjustment strap coupled to both support belts and operable to substantially simultaneously adjust both support belts in substantially the same amount about the user's body.

30. The device of claim 27, wherein at least one support belt comprises a canting mechanism coupling opposing portions of the support belt and operable to allow the opposing portions to rotate about associated pivots to allow the support belt to conform to the user's body and to synchronize the movement of the opposing portions of the support belt such that movement of one portion upward or downward requires movement of the other portion upward or downward in a substantially equivalent amount.

31. An ambulatory cyclic traction device, comprising:
two support belts configured to be positioned about a user's body, the support belts each having a front portion corresponding to a front portion of the user's body and a back portion corresponding to a back portion of the user's body;
one or more lifting mechanisms having end portions coupled to generally the front portions of the support belts and one or more lifting mechanisms having end portions coupled to generally the back portions of the support belts, the one or more front lifting mechanisms and the one or more back lifting mechanisms being adapted to apply a decompressive force to the user's body between the support belts; and
a control system coupled to the one or more front lifting mechanisms and the one or more back lifting mechanisms, the control system including a pressure transducer for monitoring pressure within the lifting mechanisms, and the control system operable to cause the one or more front lifting mechanisms and the one or more back lifting mechanisms to cyclically apply the decompressive force to the user's body through the support belts when the support belts are positioned about the user's body, such that the decompressive force is applied for a predetermined time interval during each of a series of traction cycles, whereby mobility of a portion of the user's body is restricted during each of the series of traction cycles.

32. The device of claim 31, wherein:
each of the front and back lifting mechanisms comprises a fluidic lifting mechanism; and the control system is operable to supply a fluid to pressurize each lifting mechanism to cause the lifting mechanism to cyclically apply the decompressive force.

33. The device of claim 32, wherein the control system is operable to maintain a pressure in each of the front and back lifting mechanisms during each traction cycle within a predetermined pressure range defined by a lower threshold and an upper threshold, the control system operable to supply additional fluid to the lifting mechanism in response to the pressure in the lifting mechanism falling below the lower threshold, the control system operable to reduce fluid pressure in the lifting mechanism in response to the pressure m the lifting mechanism rising above the upper threshold.

34. The device of claim 31, further comprising a common adjustment strap coupled to each of the support belts and operable to substantially simultaneously adjust the support belts in substantially the same amount about the user's body.

35. The device of claim 31, wherein at least one support belt comprises a canting mechanism coupling opposing portions of the support belt and operable to allow the opposing portions to rotate about associated pivots to allow the support belt to conform to the user's body and to synchronize the movement of the opposing portions of the support belt such that movement of one portion upward or downward requires movement of the other portion upward or downward in a substantially equivalent amount.

* * * * *

UNITED STATES PATENT AND TRADEMARK OFFICE
CERTIFICATE OF CORRECTION

PATENT NO. : 6,997,892 B2
DATED : February 14, 2006
INVENTOR(S) : Reinecke

Page 1 of 1

It is certified that error appears in the above-identified patent and that said Letters Patent is hereby corrected as shown below:

Column 13,
Line 34, delete "m" and insert -- in --.

Column 16,
Line 52, delete "m" and insert -- in --.

Signed and Sealed this

Thirteenth Day of June, 2006

JON W. DUDAS
*Director of the United States Patent and Trademark Office*